(12) United States Patent
Albert et al.

(10) Patent No.: US 8,167,913 B2
(45) Date of Patent: May 1, 2012

(54) SPINAL STABILIZATION USING BONE ANCHOR AND ANCHOR SEAT WITH TANGENTIAL LOCKING FEATURE

(75) Inventors: Todd James Albert, Narberth, PA (US); Rafail Zubok, Midland Park, NJ (US); Mikhail Kvitnitsky, Clifton, NJ (US)

(73) Assignee: Altus Partners, LLC, Newtown Square, PA (US)

( * ) Notice: Subject to any disclaimer, the term of this patent is extended or adjusted under 35 U.S.C. 154(b) by 1437 days.

(21) Appl. No.: 11/360,708

(22) Filed: Feb. 23, 2006

(65) Prior Publication Data

US 2006/0235389 A1 Oct. 19, 2006

Related U.S. Application Data

(60) Provisional application No. 60/658,227, filed on Mar. 3, 2005.

(51) Int. Cl.
*A61B 17/70* (2006.01)
(52) U.S. Cl. .......................... 606/270; 606/266; 606/306
(58) Field of Classification Search .................. 128/898; 403/76–77; 411/380, 396, 537, 910; 606/300–331, 606/266–279, 916
See application file for complete search history.

(56) References Cited

U.S. PATENT DOCUMENTS

| | | | |
|---|---|---|---|
| 5,360,431 A | 11/1994 | Puno et al. | |
| 5,474,555 A | 12/1995 | Puno et al. | |
| 5,499,983 A * | 3/1996 | Hughes | 606/267 |
| 5,584,831 A | 12/1996 | McKay | |
| 5,584,833 A | 12/1996 | Fournet-Fayard et al. | |
| 5,624,442 A | 4/1997 | Mellinger et al. | |
| 5,810,819 A | 9/1998 | Errico et al. | |
| 6,187,005 B1 * | 2/2001 | Brace et al. | 606/264 |
| 6,302,888 B1 | 10/2001 | Mellinger et al. | |
| 6,565,569 B1 | 5/2003 | Assaker et al. | |
| 6,663,635 B2 | 12/2003 | Frigg et al. | |
| 6,733,502 B2 * | 5/2004 | Altarac et al. | 606/266 |
| 6,746,449 B2 | 6/2004 | Jones et al. | |
| 6,755,830 B2 | 6/2004 | Minfelde et al. | |
| 2003/0045879 A1 * | 3/2003 | Minfelde et al. | 606/61 |
| 2003/0153911 A1 * | 8/2003 | Shluzas | 606/61 |

(Continued)

FOREIGN PATENT DOCUMENTS

WO WO2004/010881 A1 2/2004

OTHER PUBLICATIONS

ISR of PCT/US2006/06944, Feb. 23, 2006, Albert et al.

(Continued)

*Primary Examiner* — Thomas C. Barrett
*Assistant Examiner* — Larry E Waggle, Jr.
(74) *Attorney, Agent, or Firm* — Matthew B. Dernier, Esq.; Gibson & Dernier LLP

(57) ABSTRACT

A stabilization system for implantation in a patient includes: a bone anchor including a head and a shaft, the shaft extending away from the head in a bone insertion direction and being operable for connection to a bone of the patient; and a tulip including: at least one channel having an opening for receiving an elongate member, the opening being oriented in a receiving direction having at least a component thereof substantially opposite to the bone insertion direction of the anchor, and (ii) a fastening mechanism operable to apply a tangential load on the elongate member to maintain the elongate member within the channel, wherein the tangential load is transverse to at least the receiving direction.

34 Claims, 13 Drawing Sheets

U.S. PATENT DOCUMENTS

| | | |
|---|---|---|
| 2003/0187439 A1 | 10/2003 | Biedermann et al. |
| 2004/0039385 A1 | 2/2004 | Mazda et al. |
| 2004/0092930 A1 | 5/2004 | Petit et al. |
| 2004/0147929 A1 | 7/2004 | Biedermann et al. |
| 2004/0243126 A1 | 12/2004 | Carbone et al. |
| 2004/0254574 A1 | 12/2004 | Morrison et al. |
| 2005/0010216 A1 | 1/2005 | Gradel et al. |
| 2005/0049589 A1 | 3/2005 | Jackson |
| 2005/0055026 A1 | 3/2005 | Biedermann et al. |
| 2005/0187548 A1* | 8/2005 | Butler et al. .................... 606/61 |
| 2005/0228375 A1 | 10/2005 | Mazda et al. |

OTHER PUBLICATIONS

International Preliminary Report on Patentability and Written Opinion for International Application PCT/US2006/006710.

* cited by examiner

200

200

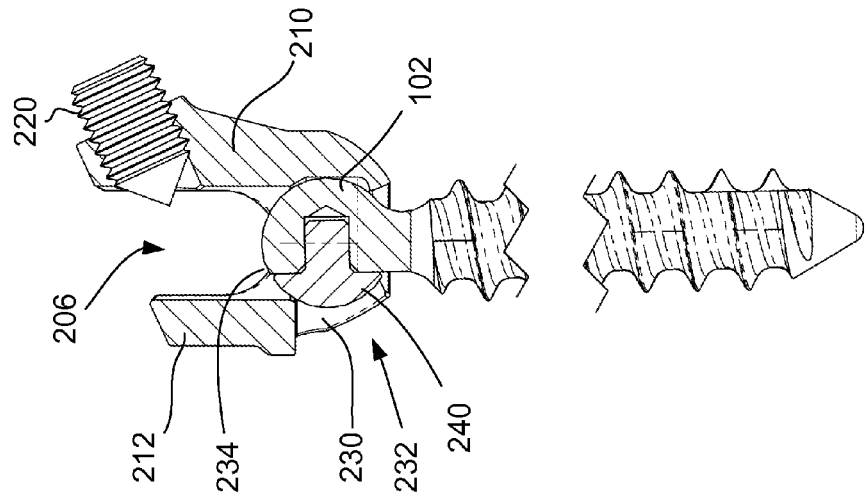
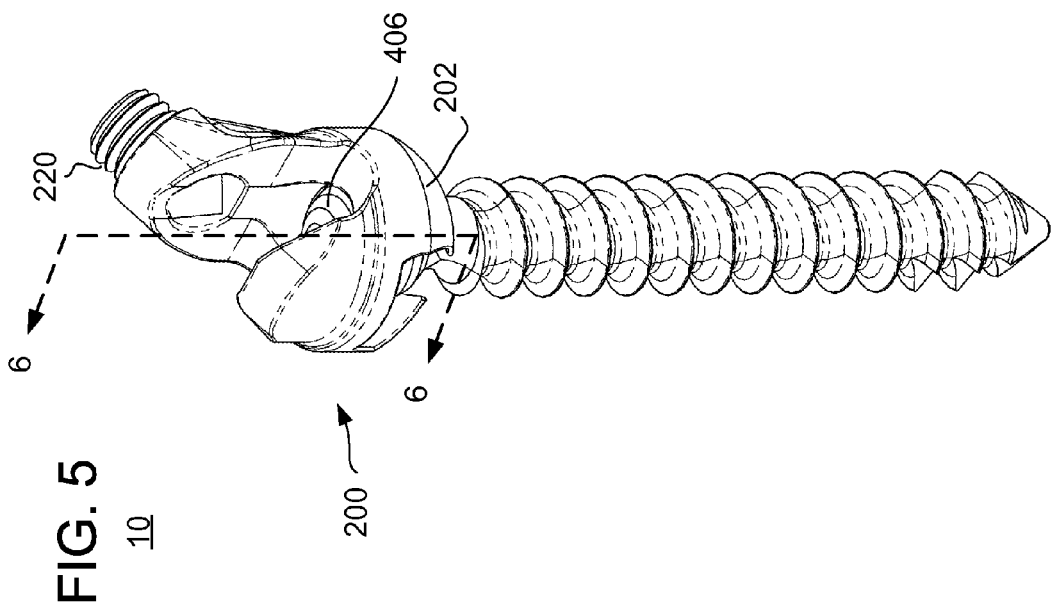

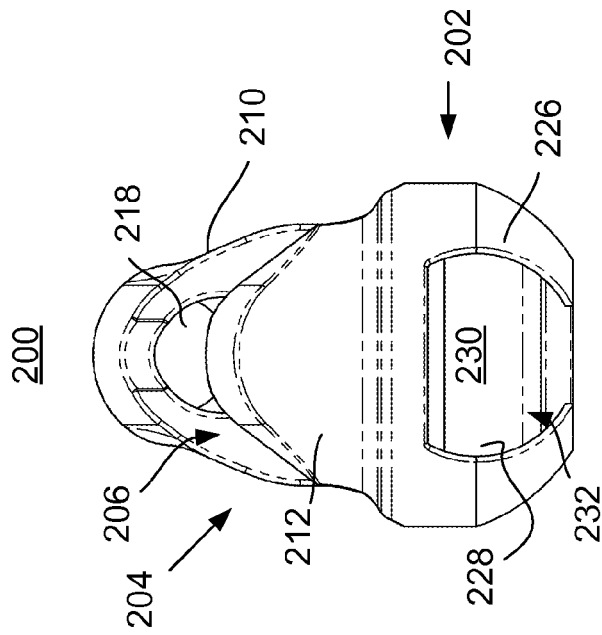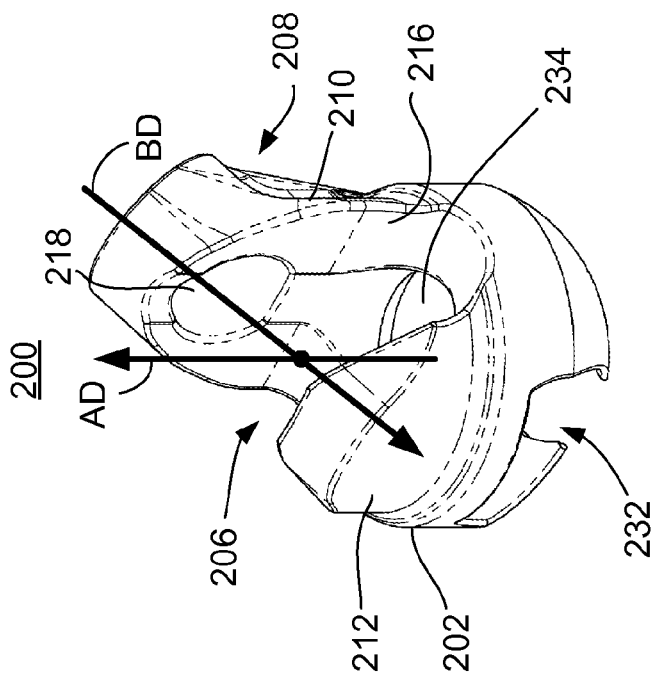

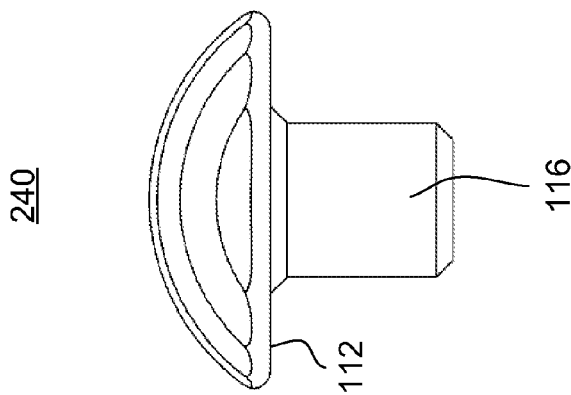
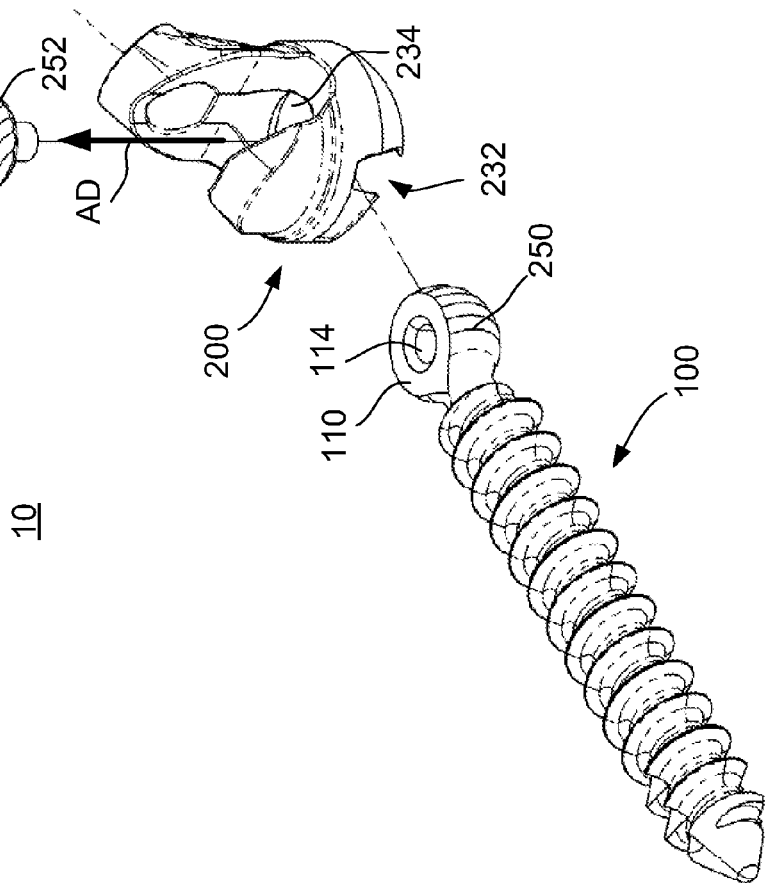

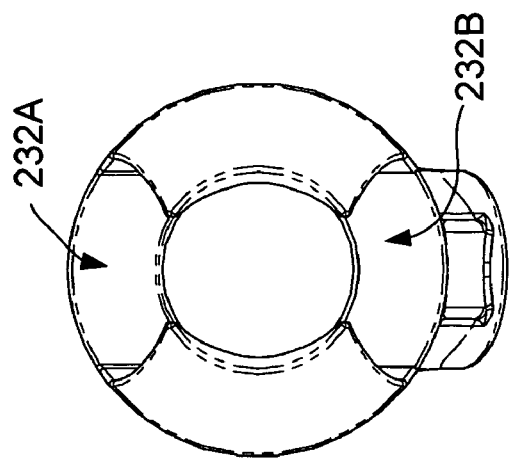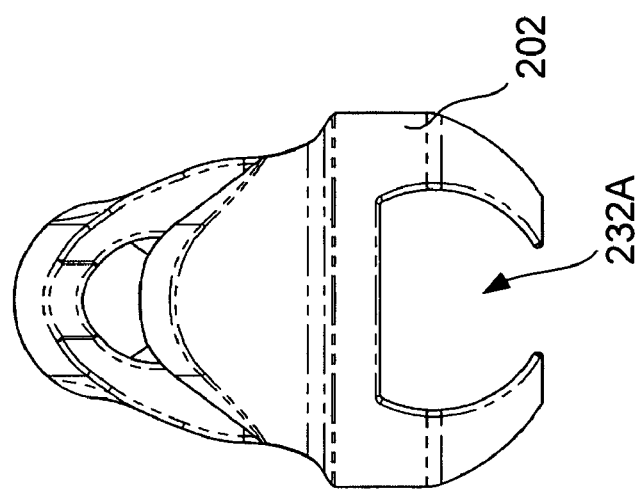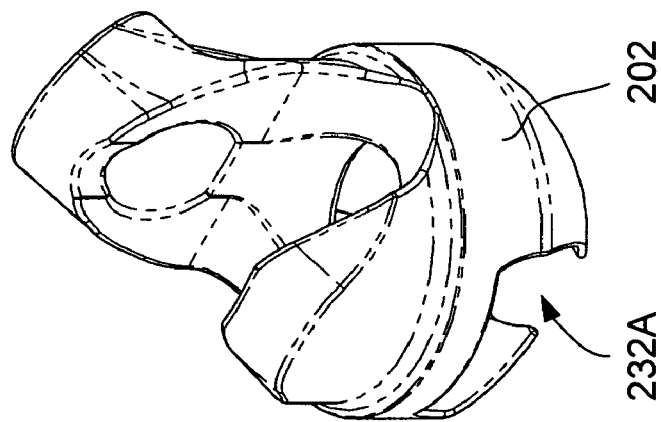

200B

200B

200B

200C

200C

200C

200D

200D

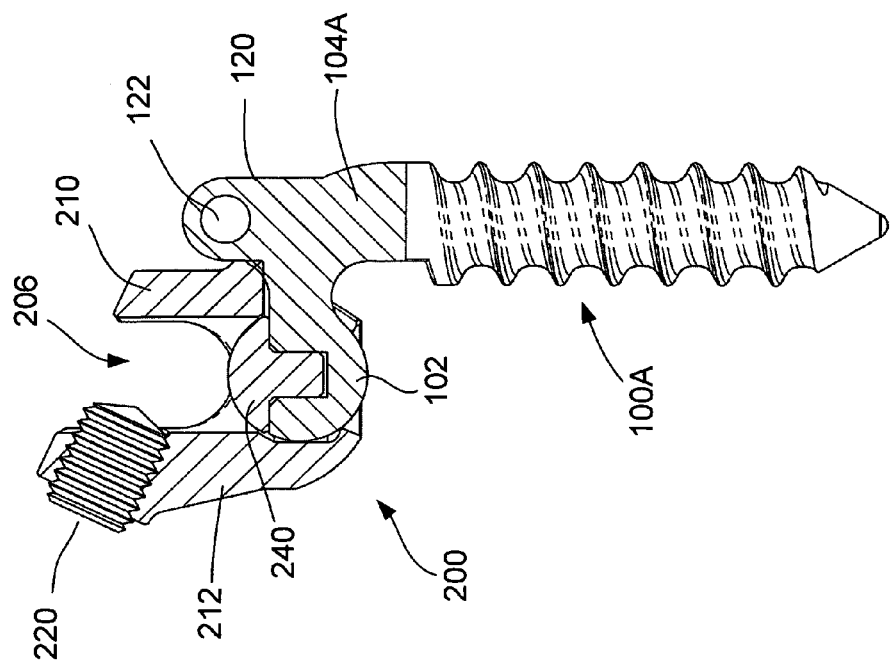
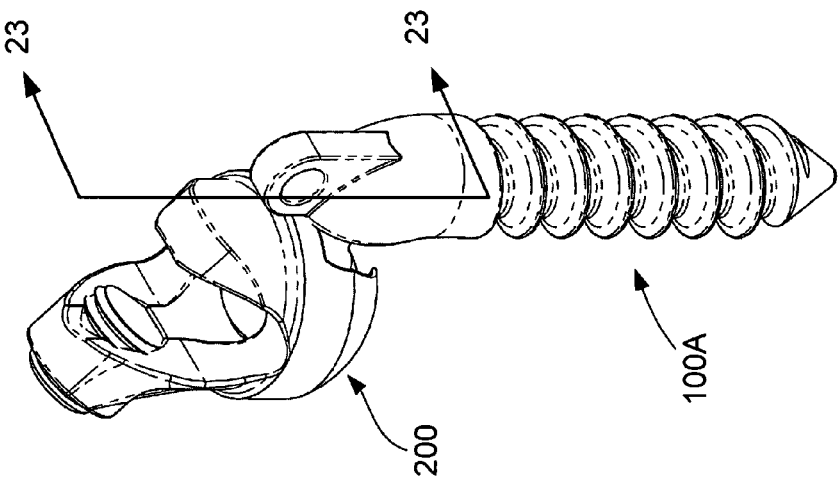

100B

10B

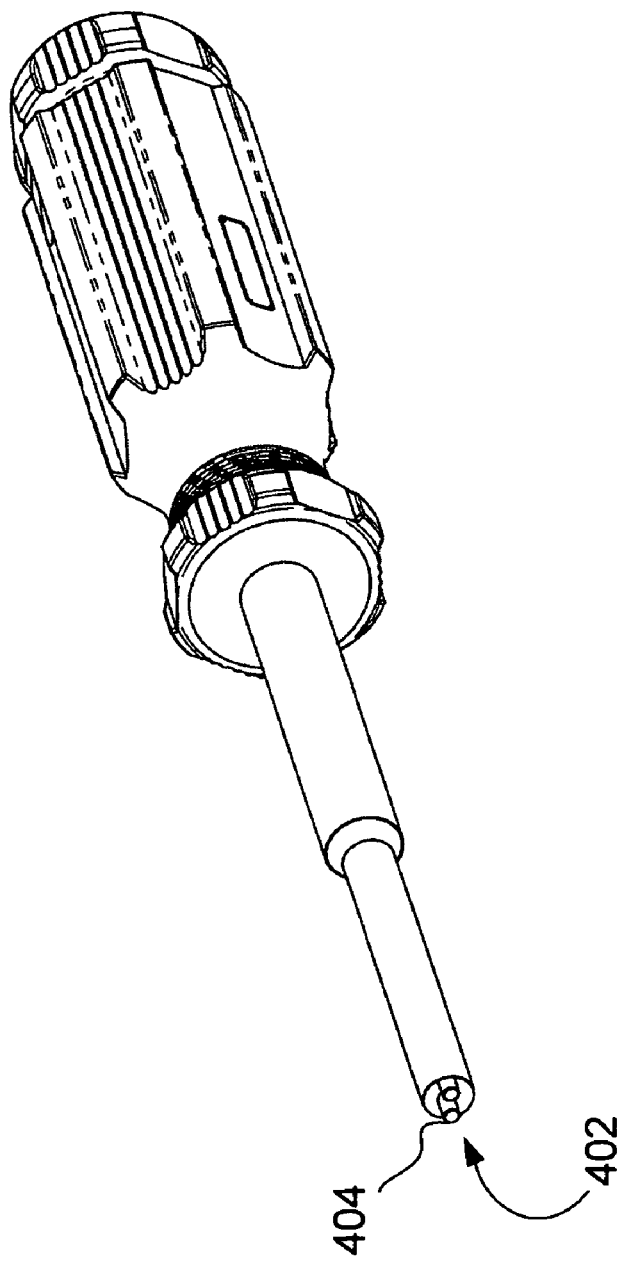

SPINAL STABILIZATION USING BONE ANCHOR AND ANCHOR SEAT WITH TANGENTIAL LOCKING FEATURE

CROSS REFERENCE TO RELATED APPLICATIONS

This application claims the benefit of U.S. Provisional Patent Application No. 60/658,227, filed Mar. 3, 2005, the entire disclosure of which is hereby incorporated by reference.

BACKGROUND OF THE INVENTION

The present invention is directed to vertebral stabilization of a spine using one or more rods anchored onto the vertebrae.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Degenerative spinal column diseases, such as disc degenerative diseases (DDD), spinal stenosis, spondylolisthesis, and so on, need surgical operation if they do not take a turn for the better by conservative management.

Various methods of spinal immobilization have been known and used during this century in the treatment of spinal instability and displacement. One treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form.

Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Internal fixation refers to therapeutic methods of stabilization which are wholly internal to the patient. External fixation in contrast involves at least some portion of the stabilization device which is external to the patient's body. Internal fixation is advantageous since the patient is allowed greater freedom with the elimination of the external portion of the device and the possibility of infections, such as pin tract infection, is reduced.

Conventional methods of spinal fixation utilize a rigid spinal fixation device to support an injured spinal part and prevent movement of the injured part. These conventional spinal fixation devices include: fixing screws configured to be inserted into the spinal pedicle or sacral of the backbone to a predetermined depth and angle, rods or plates configured to be positioned adjacent to the injured spinal part, and coupling elements for connecting and coupling the rods or plates to the fixing screws such that the injured spinal part is supported and held in a relatively fixed position by the rods or plates.

A common problem with spinal fixation is the question of how to secure the fixation device to the spine without damaging the spinal cord. The pedicles are a favored area of attachment since they offer an area that is strong enough to hold the fixation device even when the patient suffers from osteoporosis. Since the middle 1950's, methods of fixation have utilized the pedicles. In early methods, screws extended through the facets into the pedicles. Posterior methods of fixation have been developed which utilize wires that extend through the spinal canal and hold a rod against the lamina (such as the Luque system).

U.S. Pat. No. 6,187,005 (the entire disclosure of which is hereby incorporated by reference) discloses a variable angle spinal fixation system, including a rod 16 positioned along a spinal column, a bone screw 14 having a threaded end for engaging a vertebra, and a connector member 86 for connecting the bone screw 14 and the rod 16. The connector member 86 has a channel extending through side surfaces of the connector member 86 for receiving the rod, an opening 108 laterally displaced from the channel and extending through top and bottom surfaces of the connector member 86 for receiving the bone screw 14, and a fastener clamping element 70 for securing the bone screw 14 in the opening 108 at a surgeon selected angle relative to the connector member 86 and rod 16. The connector member 86 also includes an opening 28 communicating with the channel and a clamping element 30 for securing the rod 16 in the channel.

Among the problems with the system of U.S. Pat. No. 6,187,005 is that the surgeon is required to manipulate two different clamping elements to fix the position of: (i) the bone screw 14 with respect to the connector member 86 (using the screw top 70), and (ii) the rod 16 with respect to the connector member 86 (using the set screw 30). This complicates the surgical procedure and increases the likelihood that a misalignment results during the tightening process.

U.S. Pat. No. 6,755,830 discloses a lateral connector with adjustable offset for a connection between a rod and a member for fixation to the spine, comprising a component to be connected to the fixation member and provided with an extension inserted into a second component which comprises a seat for the rod and a way to immobilize the rod and the extension when placed in contact with each other. The first component comprises a head with an opening with a bearing surface of articulation cooperating with a corresponding bearing surface of the fixation member. The second component comprises an orifice for receiving the extension, permitting rotation of the second component about the extension, with the orifice intersecting the bottom of the seat to form a slot. Among the problems with the apparatus of U.S. Pat. No. 6,755,830 is that the head of the bone screw may become easily disengaged from the first component through the side opening thereof.

Therefore, conventional spinal fixation devices have not provided a satisfactory solution to the problems associated with curing spinal diseases. Additionally, existing fixation devices utilize components that are not proven to provide long-term stability and durability, and are cumbersome and overly complex in terms of how they are adjusted and/or attach to the vertebral bones.

SUMMARY OF THE INVENTION

In accordance with one or more embodiments of the present invention, a stabilization system for implantation in a patient includes: a bone anchor including a head and a shaft, the shaft extending away from the head in a bone insertion direction and being operable for connection to a bone of the patient; and a tulip including: at least one channel having an opening for receiving an elongate member, the opening being oriented in a receiving direction having at least a component thereof substantially opposite to the bone insertion direction of the anchor, and (ii) a fastening mechanism operable to apply a tangential load on the elongate member to maintain the elongate member within the channel, wherein the tangential load is transverse to at least the receiving direction.

In accordance with one or more embodiments of the present invention, a stabilization system for implantation in a patient includes: a bone anchor including a head having a contour; and a tulip including: (i) a base having an outer surface and an inner surface defining a volume for receiving the head, the contour of the head being of substantially complementary shape such that the tulip may articulate about the head, (ii) a first opening operable to permit a neck extending from the head to articulate there-within and exit the base through the first opening, and (iii) a second opening extending through the base transversely with respect to the first opening, and defining a profile that permits insertion of the head into the volume of the base at substantially one orientation of the head with respect to the profile, and does not permit insertion or removal of the head with respect to the volume of the base in substantially any other orientation of the head with respect to the profile.

In accordance with one or more embodiments of the present invention, a bone anchor includes: a head; a neck depending from the head; and a shaft extending away from the neck and being operable for connection to a bone of a patient, wherein the neck includes at least one bend such that the head is transversely oriented with respect to the shaft.

In accordance with one or more embodiments of the present invention, a tool includes: a first shaft having a proximal end and a distal end, the first shaft including a rod engagement element at the distal end that is operable to releasably and rotationally engage a stabilization rod used to interconnect a plurality of bone anchors coupled to one or more bones of a patient; a second shaft having a proximal end and a distal end, the proximal end of the second shaft being pivotally coupled to the first shaft at a position intermediate between the proximal and distal ends thereof, the distal end of the second shaft including a hitch element operable to permit connection of the tool a given one of the bone anchors, wherein: a force applied to the handle produces a torque at the proximal end of the second shaft, with the rod engagement element being at a fulcrum position, that transfers the torque into a translational force at the hitch element; and a bone to which the given bone anchor is connected is moved in response to the translational force.

In accordance with one or more further embodiments of the present invention, a bone screw, includes: a head with a contour for engagement with a tulip; and at least one keyed surface on the contour of the head such that the head is permitted to be inserted through an opening of a tulip, having a complementary profile to the keyed surface of the head, only at substantially one orientation of the head with respect to the profile.

In accordance with one or more further embodiments of the present invention a tulip for engagement with a bone stabilization rod includes: a base having an outer surface and an inner surface defining a contoured volume for receiving a head of the bone anchor, a contour of the head being of substantially complementary shape such that the tulip may articulate about the head, (ii) a first opening operable to permit a neck extending from the head to articulate there-within and exit the base through the first opening, and (iii) a second opening extending through the base transversely with respect to the first opening, and defining a profile that permits insertion of the head into the volume of the base at substantially one orientation of the head with respect to the profile, and does not permit insertion or removal of the head with respect to the volume of the base in substantially any other orientation of the head with respect to the profile.

In accordance with one or more embodiments of the present invention, a method of forming a stabilization system includes: providing a bone screw having a contoured head and a keyed surface; providing a tulip having: (i) an outer surface, an (ii) an inner surface defining a volume for receiving the head of the bone screw, and (iii) an opening extending through the base into the volume and defining a profile that permits insertion of the head into the volume of the base at substantially one orientation of the head with respect to the profile, and does not permit insertion or removal of the head with respect to the volume of the base in substantially any other orientation of the head with respect to the profile; and sliding the head through the opening into the volume in a first orientation.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIG. 5 is a perspective view of a bone stabilizer system in accordance with one or more further embodiments of the present invention;

FIG. 6 is a partial cross-sectional view of the bone stabilizer system of FIG. 5;

FIG. 7 is a perspective view of a tulip suitable for use with the bone stabilizer system of FIG. 5 and/or one or more other embodiments of the present invention;

FIG. 8 is a front view of the tulip of FIG. 7;

FIG. 9 is an exploded view of the bone stabilizer system of FIG. 5;

FIG. 10 is a side view of a plug of the bone stabilizer system of FIG. 9;

FIGS. 11, 12 and 13, are perspective, side, and bottom views, respectively, of a tulip suitable for use with one or more other embodiments of the bone stabilizer system of the present invention;

FIG. 22 is a perspective view of a bone stabilizer system in accordance with one or more further embodiments of the present invention;

FIG. 23 is a partial cross-sectional view of the bone stabilizer system of FIG. 22;

FIG. 28 is a perspective view of a tool for driving a bone stabilizer system into a bone of a patient in accordance with one or more embodiments of the present invention.

DETAILED DESCRIPTION

Figure 2:
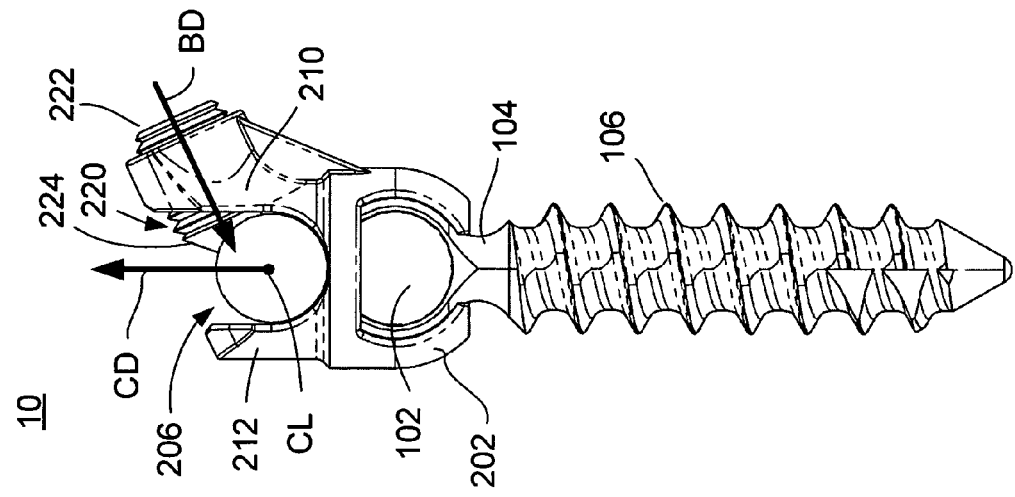
FIG. 2 is a side view of the bone stabilizer system of FIG. 1.
Figure 1:
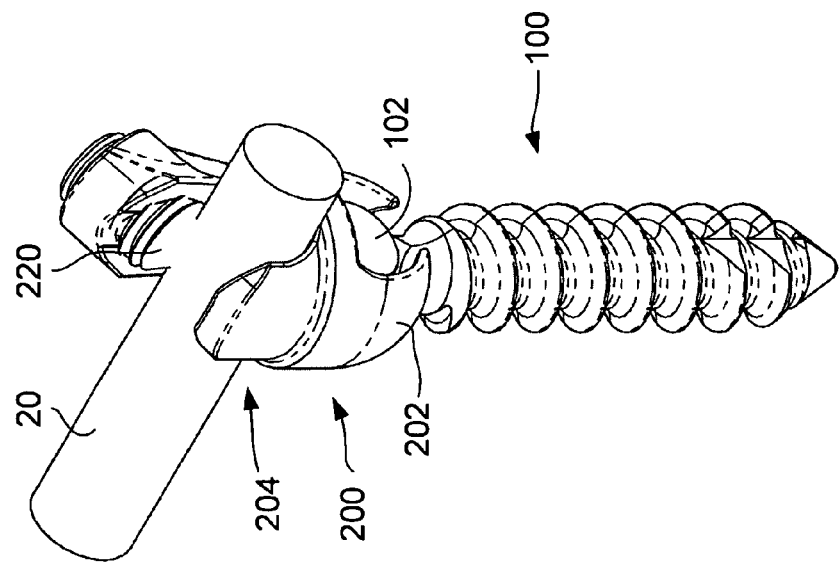
FIG. 1 is a perspective view of a bone stabilizer system in accordance with one or more embodiments of the present invention.

FIGS. 1-4 illustrate an embodiment of a spinal stabilizer system 10 in accordance with one or more aspects of the present invention. In use, it is understood that respective pairs of the stabilizing systems 10 may secure an elongate element, such as a stabilization rod, for internal fixation of respective bones of a patient, such as vertebrae of the spine.

The system 10 includes an anchor 100 and an anchor seat (or tulip) 200 that cooperate to fix a portion of a rod 20 to a bone. The bone anchor 100 includes a head 102, a neck 104, and a shaft 106, where the neck 104 interconnects the head 102 and the shaft 106. The shaft 106 extends away from the head 102 and is operable for connection to the bone of the patient. For example, the shaft 106 may include threads that may engage a bore made in the bone such that the anchor 100 is secured to the bone of the patient. In this embodiment, the bone anchor 100 and the tulip 200 are two separate pieces that are coupled together. It is noted that in one or more other embodiments, however, the bone anchor 100 may be integrally formed with the tulip 200.

The tulip 200 includes a base 202 that is operable to engage the head 102 of the anchor 100 and a crown 204 that is operable to engage the stabilization rod 20. The crown 204 includes a rod engagement element, which may be implemented utilizing at least one channel 206 having an opening for receiving the rod 20. In one or more embodiments, the opening may be oriented in a receiving direction that is substantially opposite to a direction in which the shaft 106 of the anchor 100 is driven or secured into the bone. As the tulip 200 may articulate with respect to the head 102 of the bone anchor 100, it is noted that the receiving direction may be virtually exactly opposite to the direction in which the shaft 106 of the anchor 100 is driven or secured into the bone in a limited number (e.g., one) of articulation positions. In other words, at least a vector component of the receiving direction is substantially opposite to the bone insertion direction of the anchor 100. In other articulation positions of the tulip 200 with respect to the head 102, the receiving direction may be only generally opposite (e.g., transversely directed) with respect to the shaft 106 direction.

The crown 204 may also include a fastening mechanism 208 that is adapted to apply a tangential load on the rod 20 to maintain the rod 20 within the channel 206. In this regard, the channel 206 may be defined by first and second substantially oppositely directed walls 210, 212 that are coupled together by a bridging region 214. In one or more embodiments, the walls 210, 212 and the bridging region 214 cooperate to define a generally U-shaped surface 216. It is understood that a portion of the U-shaped surface 216 in the area of the bridging region 214 define a partially cylindrical portion of the surface 216 that may be sized and shaped to compliment the contour of the rod 20.

The fastening mechanism 208 may include a threaded base element 218 that is integral with the tulip, and a threaded locking element 220 operable for threading engagement with the base element 218. The base element 218 is directed transversely toward the channel 206 such that the locking element 220 directly or indirectly urges the longitudinal stabilization rod 20 against portions of both the second wall 212 and the bridging region 214 of the channel 206 in response to turning with respect to the base element 218.

By way of example, the base element 218 may include a threaded bore that extends through the first wall 210 and into the channel 206. The locking element 220 may be a threaded shaft, which includes a proximal end 222 and a distal end 224, where the distal end 224 is operable to extend into the channel 206 in response to turning the locking element 220 into the bore 218. The bore 218 is preferably oriented such that the distal end 224 of the locking element 220 urges the rod 20 against the second wall 212 (and possibly also against a portion of the bridging region 214 of the channel 206) in response to turning the locking element 220 into the bore 218.

Alternatively, the base element 218 may include a threaded shaft integrally formed on the first wall 210. The locking element 220 may include a threaded nut and a sleeve, where the sleeve is slideable over the threaded shaft. The nut is operable to force the sleeve to engage and urge the rod 20 against portions of both the second wall 212 and the bridging region 214 of the channel 206 in response to turning the nut with respect to the threaded shaft.

Figure 4:
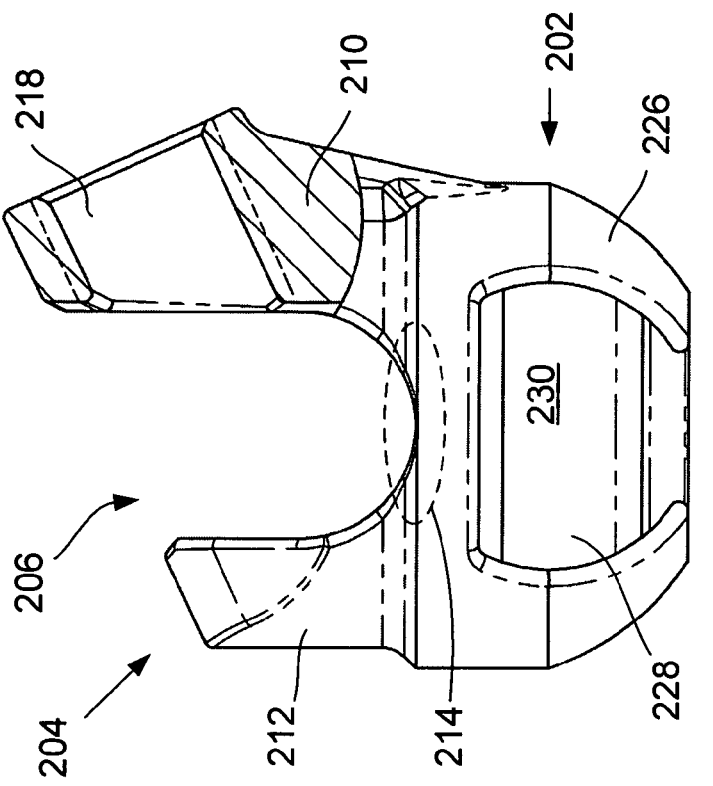
FIG. 4 is a side view of the tulip of FIG. 3.

For simplicity, the remainder of this disclosure will assume an embodiment where the fastening mechanism 208 includes a threaded bore 218 and a threaded shaft (locking element) 220. The bore 218 is preferably positioned within the first wall 210 to achieve certain desirable orientations with respect to the rod 20 when it is received in the channel 206. As best seen in FIGS. 2 and 4, the bore 218 extends in an axial direction BD that is oblique to a receiving direction CD of the channel 206. In general, the axial direction BD extends at least one of: transverse to, perpendicular to, and offset from, a center line CL of the rod 20 (opposite the bridging region 214 of the channel 206). The axis BD of the bore 218 may also extend substantially perpendicularly to, and offset from, the centerline CL of the rod 20. This orientation advantageously provides the aforementioned tangential load on the rod 20, which urges the rod 20 both toward the second wall 212 and downward toward the bridging region 214. In this embodiment, the load applied by the locking element 220 is transverse to both the bone insertion direction of the anchor 100 and the receiving direction CD of the channel 206 in substantially all articulations of the tulip 200 about the head 102.

Reference is now made to FIGS. 5-8, which illustrate further features of the stabilization system 10. FIG. 5 is a perspective view of the stabilization system 10 without the rod 20 within the channel 206. FIG. 6 is cross-sectional view of the stabilization system 10 of FIG. 5 taken through line 6-6. FIGS. 7-8 are perspective and front views, respectively, of the tulip 200.

As best seen in FIG. 8, the base 202 includes an outer surface 226 and an inner surface 228 defining a volume 230, which cooperate to form an anchor engagement element for receiving the head 102 of the anchor 100. In a preferred embodiment, the inner surface 228 of the base 202 and a surface of the head 102 are of substantially complimentary shapes such that the tulip 200 may articulate about the head 102 and achieve various desirable orientations at which to engage the rod 20, and resultant therapeutic effects. For example, the head 102 may have a generally (or partially) spherical shape, while the inner surface 228 may define a generally cylindrical contour. The base 202 also includes at least one opening (or aperture) 232 extending through the surfaces 226, 228 of the base 202 to provide access to the volume 230. The opening 232 circumscribes a profile that permits insertion of the head 102 into the volume 230 of the base 202. It is noted that tulip 200 of FIGS. 5-8 is substantially the same as the tulip 200 discussed above with respect to FIGS. 1-4. As best seen by comparing FIGS. 3 and 7, however, the tulip 200 of FIGS. 5-8 includes the opening 232 in a front direction as compared with the opening 232 in the side direction in FIG. 3.

In one or more embodiments, the base 202 and the crown 204 are adapted such that application of the load by the locking element 220 fixes both the rod 20 with respect to the tulip 200 and the tulip 200 with respect to the anchor 100. As best seen in FIG. 6, the volume 230 of the base 202 is in communication with the channel 206 such that a portion of the head 102 extends into the channel 206. In other words, the inner surface 228 of the base 202 intersects the U-shaped surface of the channel 206. The intersection of the volume 230 and the channel 206 define an aperture 234 that permits a portion of the head 102 to extend into the channel 206. The load applied to the rod 20 by the locking element 220 biases the rod 20 against the U-shaped surface of the channel 206 as well as against the head 102 in order to fix both the rod 20 with respect to the tulip 200 and to fix the tulip 200 with respect to the anchor 100. More particularly, the load applied to the rod 20 is at least partially transferred to the head 102 such that the head 102 is biased against portions of the inner surface 228 of the base 202, thereby fixing the head 102 within the volume 230.

Figure 3:
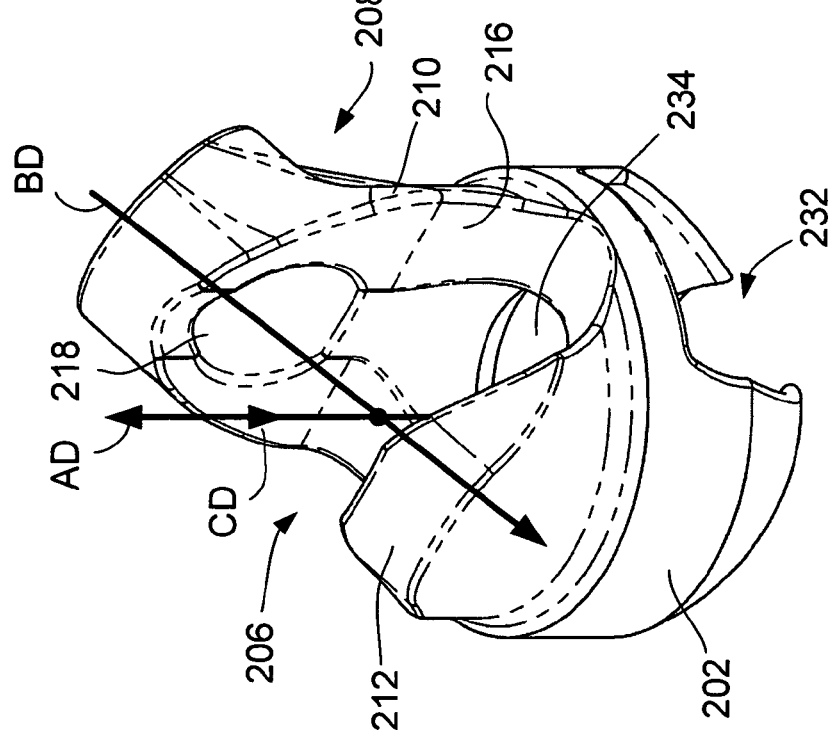
FIG. 3 is a perspective view of a tulip suitable for use with the bone stabilizer system of FIG. 1 and/or one or more other embodiments of the present invention.

As best seen in FIGS. 3 and 7, the aperture 234 defines a central axis AD, which in this embodiment is substantially co-axial with respect to the bone insertion direction of the shaft 106 of the anchor 100. In this embodiment, the bore 218, the volume 230, and the aperture 234 are substantially aligned such that the longitudinal axis BD of the bore 218 intersects the central axis AD of the aperture 234.

Reference is now made to FIGS. 9 and 10, which illustrate features of the stabilization system 10 that permit the head 102 of the anchor 100 to be captured within the volume 230 of the tulip 200. The profile of the opening 232 extending through the base 202 permits insertion of the head 102 into the volume 230 of the base 202 at substantially one orientation of the head 102 with respect to the profile. Conversely, the profile of the opening 232 does not permit insertion or removal of the head 102 with respect to the volume 230 of the base 202 in substantially any other orientation of the head 102 with respect to the profile. Preferably, the contour of the head 102 includes at least one keyed surface 110 and the profile of the opening 232 includes a keyed portion complementary to the keyed surface 110 of the head 102 such that insertion of the head 102 into the volume 230 of the base 202 is permitted only at substantially one orientation of the head 102 with respect to the profile.

In one or more embodiments, the bone anchor 100 may further include a plug element operatively connectable to the head 102 after insertion into the volume 230 of the tulip 200. The plug element is operable to alter the keyed surface 110 of the head 102 such that removal of the head 102 with respect to the volume 230 of the base 202 in substantially any orientation of the head 102 with respect to the profile of the opening 232 is prohibited.

In one or more embodiments, the bone anchor 100 may include a plug 240 that is connectable to the head 102. The head 102 includes a contour, while the plug 240 includes a complimentary contour. The contour of the head 102 is sized and shaped such that the profile of the opening 232 through the base 202 permits insertion of the head 102 into the volume 230 (without the plug 240 connected to the head 102). As will be demonstrated hereinbelow, the profile of the opening 232 preferably does not permit insertion of the head 102 when the plug 240 is connected to the head 102. In addition, once the head 102 is inserted into the volume 230 and the plug 240 is connected to the head 102, the profile of the opening 232 does not permit removal of the head 102, such that the head 102 is fully captured within the volume 230.

As illustrated, the head 102 includes a first partial spherical contour, which defines a cut-off spherical contour including a first substantially planar surface 110. The plug 240 includes a second partial spherical contour, which defines a second cut-off spherical contour including a second substantially planar surface 112. One of the first and second surfaces 110, 112 (in this example the surface 110) includes a bore 114 and the other of the surfaces 110, 112 (in this case surface 112) includes a mating post 116. The plug 240 may be operatively coupled to the head 102 by engaging the post 116 into the bore 114. In one or more embodiments, the bore 114 and the post 116 may be sized and shaped to achieve a substantial press fit in which the plug 240 may be well secured to the head 102. In alternative embodiments, additional adhesive and/or other coupling mechanisms may be employed to ensure that the plug 240 does not become inadvertently disengaged from the head 102 once it is in place.

As best seen in FIG. 8, the profile of the opening 232 corresponds to a cross-section of the head 102 taken perpendicularly through the surface 110, particularly through a plane of maximal diameter of the head 102. Thus, the profile of the opening 232 is sized and shaped to permit the head 102 to slide therethrough into the volume 230 when in a first orientation. In this example, such orientation is substantially transverse with respect to the central axis AD of the aperture 234. Once the head 102 is slid into the volume 230, movement of the anchor 100 into other orientations prevents the head from leaving the volume 230 due to the profile of the opening 232. Once the plug is coupled to the head 102, the profile of the opening 232 prevents the head 102 from leaving the volume when in any orientation (i.e., the head 102 is completely captured within the tulip 200).

In one or more embodiments, the aperture 234 may be sized and shaped to permit the plug 240 to pass therethrough and couple to the head 102, as is illustrated in FIG. 9. In alternative embodiments, the opening 232 may be sized and shaped to permit the plug 240 to pass therethrough and couple to the head 102.

In one or more further embodiments, the keyed surface 110 may be such that the contour of the head 102 and the profile of the opening 232 are sized such that a shrink fit function is achieved. For example, the profile of the opening 232 may be sized smaller than the contour of the head 102 would suggest such that when the head 102 and the tulip are at least close to the same temperature (e.g., at an equilibrium temperature condition) insertion or removal of the head 102 with respect to the volume 230 of the base 202 in substantially any orientation of the head 102 with respect to the profile of the opening 232 is prohibited. (It is noted that a substantially less radical flat surface 110 may be employed, such as by significantly decreasing a surface area of the flat surface 110.) For a shrink fit insertion of the head 102 into the volume 230 of the tulip 200, the head 102 and the tulip 200 may be taken to different temperatures (a non-equilibrium temperature condition) such that the profile of the opening 232 is large enough to receive the head 102 into the volume 230 of the base 202 (at least in one orientation of the head 102 with respect to the profile of the opening 232). Thereafter, the temperatures of the head 102 and the tulip 200 may be equalized, whereby the head 102 is fully captured within the volume 230.

In one of more embodiments, the head 102 and/or the plug 240 may include a friction enhancement feature. The friction enhancement feature is preferably operable to facilitate fixed orientations among the components of the stabilization system 10 when the locking element 220 is driven through the bore 218 and engages the rod 20. By way of example, the friction enhancement feature 250 on the head 102 and friction enhancement feature 252 on the plug 240 may include ridges, grooves, protrusions, dimples, cross-hatching, knurling, etc. As illustrated in FIGS. 9- 10, the head 102 and the plug 240 include grooves. In still further embodiments, the rod 20 may also include such friction enhancement features.

Figure 16:
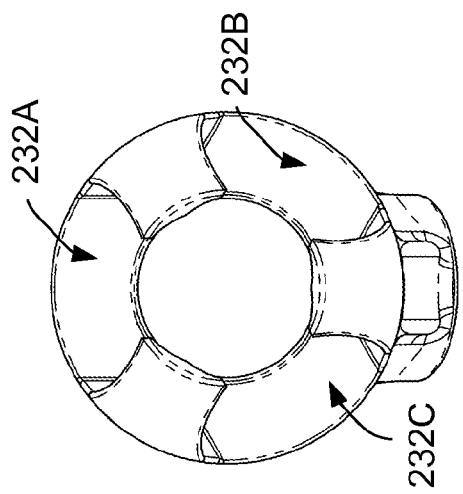
FIGS. 14, 15 and 16, are perspective, side, and bottom views, respectively, of an alternative tulip suitable for use with one or more other embodiments of the bone stabilizer system of the present invention.
Figure 15:
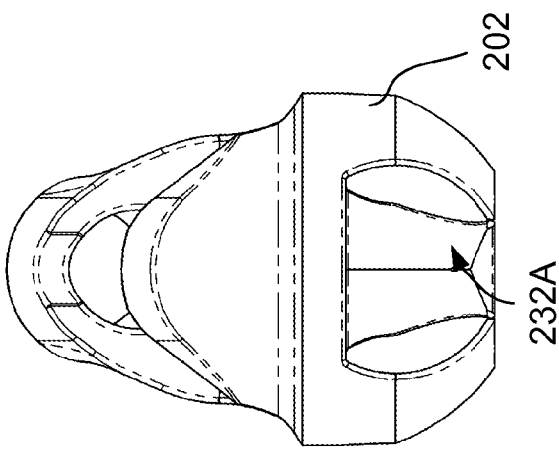
Figure 14:
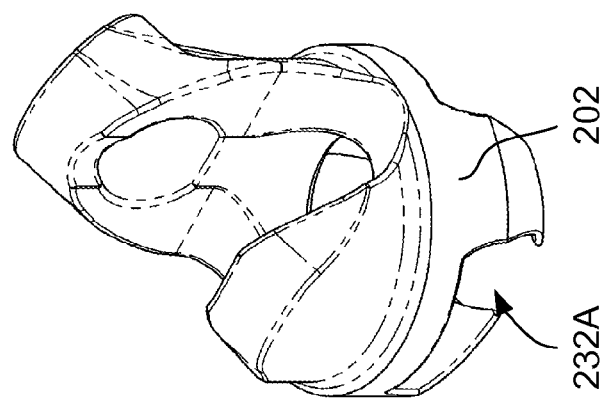

Reference is now made to FIGS. 11, 12 and 13, which are perspective, side, and bottom views of a tulip 200A having an alternative design. In particular, the base 202 includes a plurality of openings 232A, 232B. In this example, the openings 232A, 232B are disposed on opposite sides of the base 202. In alterative embodiments, the openings 232A, 232B may be transverse with respect to one another. Notably, the lower opening (through which the neck 104 of the bone anchor 100 extends is in communication with at least one (and preferably both) of the openings 232A, 232B. Preferably, at least one of the openings 232A, 232B has the profile for accommodating insertion of the head 102 into the volume 230. The other opening 232A, 232B need not include such a profile, however it is preferred that the openings 232A, 232B permit the neck 104 of the head 102 to enter depending on the orientation of the shaft 106t with respect to the tulip 200. This accommodates more radical articulations of the tulip 200 with respect to the bone anchor 100. With reference to FIGS. 14, 15 and 16, an alternative tulip 200B may employ a base 202 having three openings 232A, 232B, 232C, disposed substantially equidistant from one another about the base 202. Those skilled in the art will appreciate that many other alternative designs may be determined from the description herein.

Figure 19:
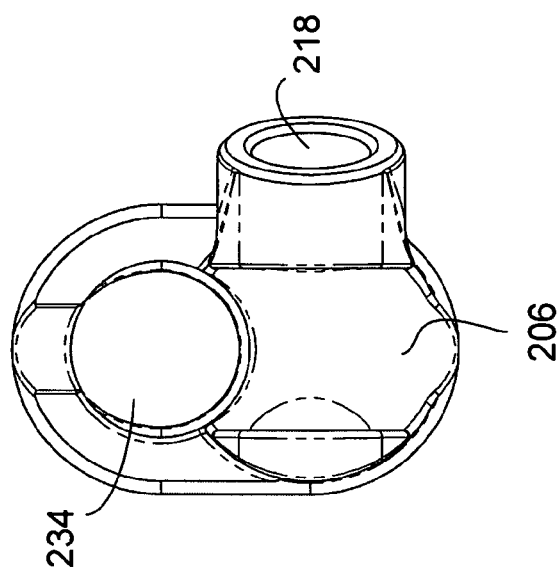
FIGS. 17, 18, and 19 are perspective, cross-sectional, and top views, respectively, of an alternative tulip suitable for use with one or more other embodiments of the bone stabilizer system of the present invention.
Figure 18:
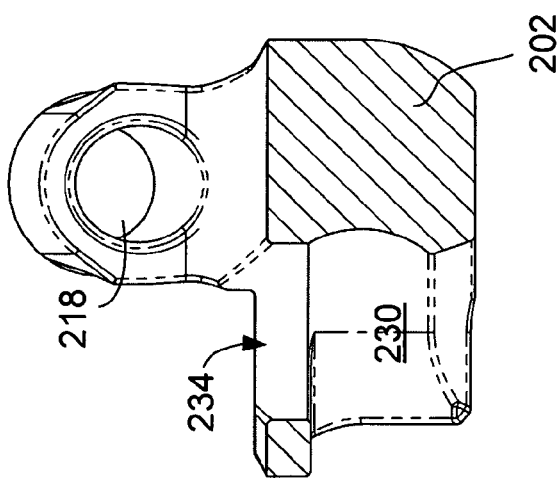
Figure 17:
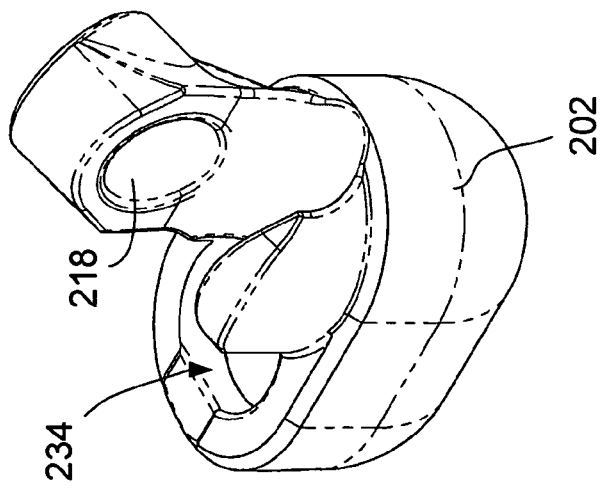
Figure 21:
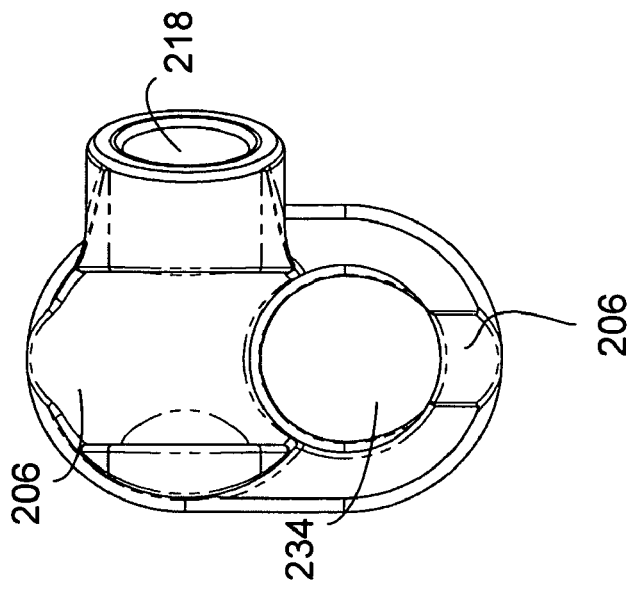
FIGS. 20 and 21 are perspective and top views, respectively, of an alternative tulip suitable for use with one or more other embodiments of the bone stabilizer system of the present invention.
Figure 20:
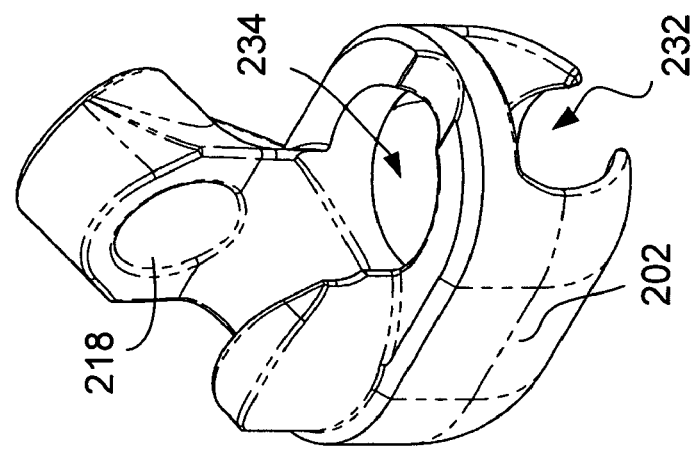

Reference is now made to FIGS. 17, 18, and 19, which are perspective, cross-sectional, and top views of an alternative tulip 200C in accordance with one or more further aspects of the present invention. The tulip 200C shares some similar features with respect to the prior embodiments discussed hereinabove. The tulip 200C, however, also includes a feature in which the bore 218 is offset from the volume 230 of the base 202 and the aperture 234. In other words, the longitudinal axis BD of the bore 218 is offset from the central axis AD of the aperture 234. This is in contrast, for example, to the respective tulips 200 illustrated in FIGS. 3 and 7. The offset feature, among other things, permits the anchor 100 to be positioned in a bone such that interference of the insertion of the locking element 220 is avoided, which may be a desirable feature in some anatomical applications. As illustrated in the embodiment of the tulip 200D shown in FIGS. 20 and 21, the longitudinal bore 218 may be offset to one side or the other of the aperture 234 depending on the particular anatomical situation.

Reference is now made to FIGS. 22 and 23, which illustrate a stabilization system 10A in accordance with one or more further embodiments of the present invention. FIG. 22 is a perspective view of the stabilization system 10A, while FIG. 23 is a cross-sectional view of the stabilization system 10A taken through line 23-23. The stabilization system 10A includes a bone anchor 100A and a tulip 200, it being understood that any of the aforementioned tulips may be employed in combination with the bone anchor 10A.

The bone anchor 100A includes many of the same features as discussed hereinabove with respect to the bone anchor 100. In addition, the anchor 100A may include a neck 104A having a bend such that the head 102 is transversely oriented with respect to the shaft 106. While the bend may take on any angle, a preferred angle is substantially 90 degrees. As shown, the transverse nature of the neck 104A offsets the head 102 from the shaft 106. The offset feature, among other things, permits the anchor 100A to be positioned in a bone such that interference of the tulip 200, the locking element 220, and/or the rod 20 is avoided, which may be a desirable feature in some anatomical applications.

In addition, the bone anchor 100A may include a hitch element 120 depending from the neck 104A. The hitch element 120 is operable to permit connections of a tool, such as the tool 300 illustrated in FIG. 24. The tool 300 may be utilized to connect to the hitch element 120 to permit manipulation of the anchor 100A and thus the position of the bone into which the anchor 100A is connected. In one or more embodiments, the hitch element 120 may include an ear member having an aperture 122 at least partially extending therethrough, where the ear is releasably engageable with the tool 300. (Further details regarding the tool 300 will be discussed hereinbelow.) When the neck 104A includes a bend (such as the 90 degree bend illustrated), the hitch may depend from the neck 104A in a substantially in-line orientation with respect to the shaft 106. Those skilled in the art will appreciate that the hitch 120 may be utilized with the bone anchor 100A without the bend in the neck 104. In such embodiments, however, the head 102 is substantially in-line with the shaft 106; hence, the hitch element 120 would have to extend transversely from the neck 104 in an out-of-line orientation with respect to the shaft 106.

Figure 24:
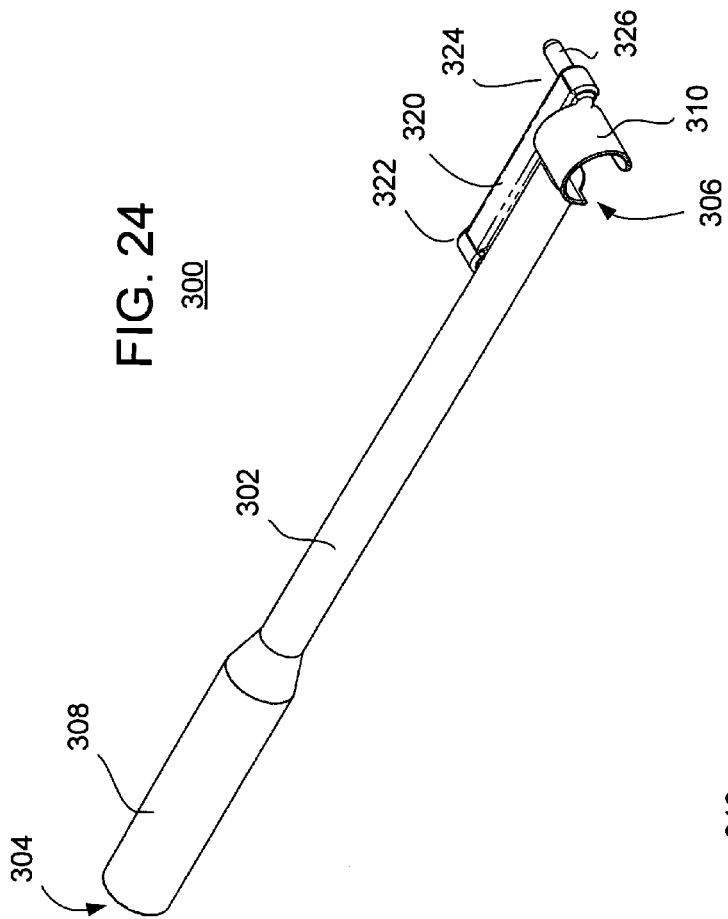
FIG. 24 is a perspective view of a tool for manipulating a bone stabilizer system in accordance with one or more embodiments of the present invention.
Figure 25:
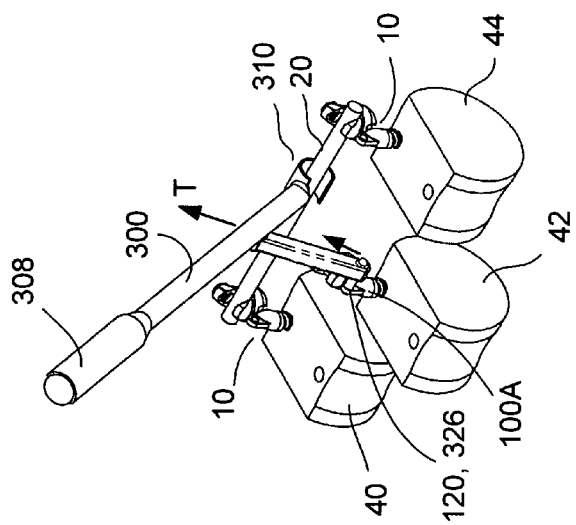
FIG. 25 is a view of the tool of FIG. 24 in the process of manipulating a bone stabilizer system.

With reference to FIGS. 24 and 25, the tool 300 includes a first shaft 302 having a proximal end 304 and a distal end 306. The first shaft 302 includes a handle 308 at the proximal end 304 and a rod engagement element 310 at the distal end 306. The rod engagement element 310 is operable to releasably and rotationally engage the stabilization rod 20. The rod engagement element 310 may include a hook that is sized and shaped to releasably and rotationally engage the stabilization rod 20. The tool 300 also includes a second shaft 320 having a proximal end 322 and a distal end 324. The proximal end 322 of the second shaft 320 is pivotally coupled to the first shaft 302 at a position intermediate between the proximal and distal ends 304, 306 thereof. The distal end 324 of the second shaft 320 includes a hitch element 326 that is operable to permit connection of the tool 300 to the hitch element 120 of the bone anchor 10A. The hitch element 326 may include a pin that is sized and shaped to engage the aperture 122 of the hitch element 120. Preferably, the pin extends transversely with respect to the second shaft 320 such that it may engage the aperture 122.

More particular reference is now made to FIG. 25, which shows the tool 300 in use. A plurality of stabilization systems 10 have been coupled to respective vertebrae 40, 42, and 44 of a patient. A rod 20 engages respective tulips 200 of a pair of outermost systems 10. A third bone anchor 100A located between the outermost systems 10 is out of position due to the displacement of the vertebrae 42, such that the tulip 200 thereof cannot readily engage the rod 20. The tool 300 may be coupled to the rod 20 by way of the rod engagement element 310, and engage the intermediate bone anchor 100A by way of the hitch elements 120, 326. A force F applied to the handle 308 of the tool 300 produces a torque T at the proximal end 322 of the second shaft 320, with the rod engagement element 310 being at a fulcrum position. The torque T is transferred into a translational force Tr at the hitch elements 120, 326 such that the bone anchor 100A may move the vertebrae 42 into a better position to connect the tulip 200 to the rod 20.

Figure 27:
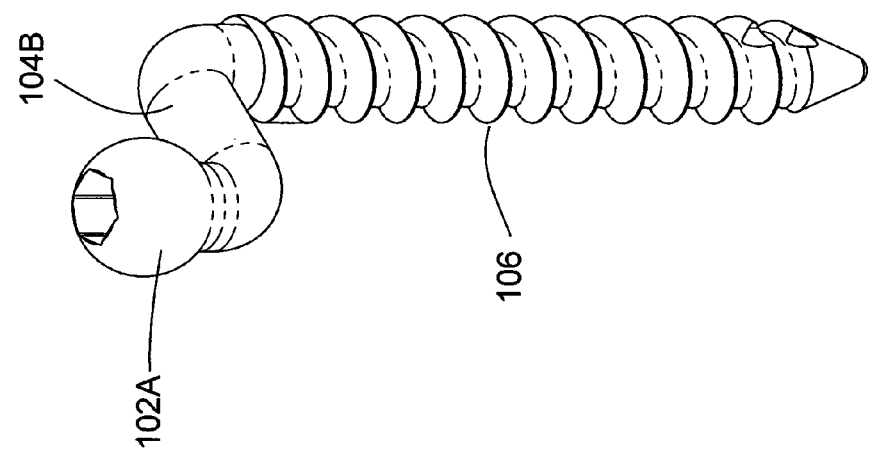
FIG. 27 is a perspective view of a bone screw suitable for use in the stabilizer system of FIG. 26 and/or one or more other embodiments of the present invention.
Figure 26:
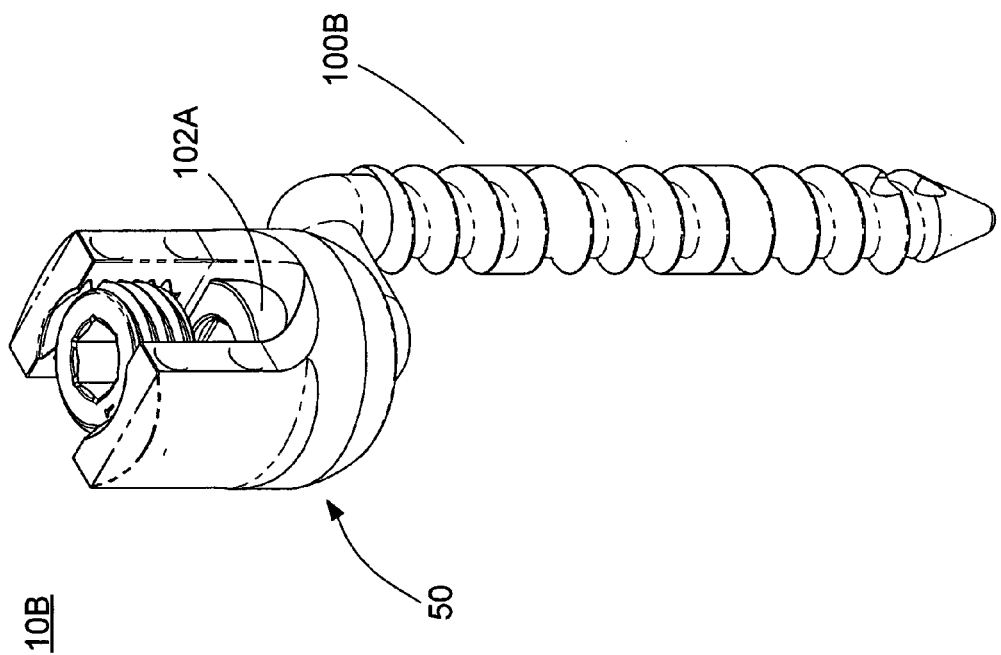
FIG. 26 is a perspective view of a bone stabilizer system in accordance with one or more further embodiments of the present invention.

Reference is now made to FIGS. 26 and 27, which illustrate a stabilization system 10B in accordance with one or more further embodiments of the present invention. FIG. 26 is a perspective view of the stabilization system 10B including a conventional tulip 50, while FIG. 27 is a perspective view of a bone anchor 100B. The bone anchor 100B includes a head 102A of generally spherical construction, a neck 104B, and a shaft 106 extending away from the neck 104B. The neck 104B includes a re-entrant bend such that the head 102A is offset from the shaft 106. While the re-entrant bend may take on numerous configurations, one embodiment includes a pair of 90 degree turns as shown. One or more further embodiments may employ a pair of bends that are of substantially equal angles (other than 90 degrees). As shown, the offset nature of the neck 104A offsets the head 102A from the shaft 106 and, among other things, permits the anchor 100B to be positioned in a bone such that interference of the tulip 50 and/or the rod 20 is avoided, which may be a desirable feature in some anatomical applications.

Reference is now made to FIG. 28, which is a perspective view of a tightening tool 400 that may be utilized to drive the anchor 100 into the bone. The tool 400 includes a distal end 402 employing an engagement element 404. In this embodiment, the engagement element includes a spanner (a pair of pins) that may engage a corresponding recess or recesses of the anchor 100. It is noted that the engagement element 404 may take on other designs, such as a hex driver, a star driver, a torx driver, a flat head driver, a Phillips driver, a square driver, etc. With reference to FIG. 5, the recess or recesses may be preferably disposed at the end 406 of the head 102 of the anchor 100. Rotational torque applied to the tool 400 translates into a driving force that causes the anchor 100 to thread through a bore in the bone. The recess or recesses may be machined or drilled into the end 406 of the head 102 prior to or after assembling the anchor 100 to the tulip 200 depending on whether such recess or recesses would interfere with the bore 114 and post 116.

Preferably the components discussed above are formed from CP Titanium or Titanium Alloy, Stainless Steel, Cobalt Chromium Alloy, Plastics and/or other biologically acceptable materials. The tools of FIGS. 24-25 and 28 may be formed from non-biologically acceptable materials, such as steel. The portions of the device may be produced in the range of sizes and length adequate to the requirements.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stabilization system for implantation in a patient, comprising:
    a bone anchor including a head and a shaft, the shaft extending away from the head in a bone insertion direction and being operable for connection to a bone of the patient; and
    a tulip including:
        at least one channel defined by first and second substantially oppositely directed walls, the channel having an opening for receiving an elongate member, the opening being oriented in a receiving direction having at least a component thereof substantially opposite to the bone insertion direction of the anchor,
        a fastening mechanism operable to apply a tangential load on the elongate member to maintain the elongate member within the channel, wherein the tangential load is transverse to at least the receiving direction;
    a base including an anchor engagement element defined by a volume formed from an inner and an outer surface of the base to couple to the head of the anchor, such that the anchor engagement element and the head are of substantially complementary shape to permit articulation of the tulip about the head,
    the channel and the base are arranged such that a central, longitudinal axis of the base coincides with a central, longitudinal axis of the channel,
    wherein the fastening mechanism is operable to apply the tangential load on the elongate member such that both the elongate member is fixed with respect to the tulip and the tulip is fixed with respect to the anchor and the volume of the anchor engagement element is in communication with the channel such that a portion of the head extends into the channel.

2. The stabilization system of claim 1, wherein the first and second substantially oppositely directed walls are coupled together by a bridging region, which walls cooperate to define a generally U-shaped surface.

3. The stabilization system of claim 2, wherein: the fastening mechanism includes: (i) a threaded base element that is integral with the tulip, and (ii) a threaded locking element operable for threading engagement with the base element; and the base element is directed transversely toward the channel such that the locking element directly or indirectly urges the elongate member against portions of both the second wall and the bridging region of the channel in response to turning with respect to the base element.

4. The stabilization system of claim 3, wherein the base element includes a threaded bore opening through the first wall into the channel, and the threaded locking element is operable to extend into the channel in response to turning within the threaded bore.

5. The stabilization system of claim 4, wherein the threaded locking element includes a threaded shaft having a distal end operable to extend into the channel and engage the elongate member.

6. The stabilization system of claim 3, wherein the base element is directed toward the channel oblique to the receiving direction of the channel.

7. The stabilization system of claim 3, wherein: the elongate member includes, in use, a center line extending substantially parallel to and spaced from the bridging surface of the channel; and the base element defines an axis extending at least one of: transverse to, perpendicular to, and offset from, the center line of the elongate member opposite the bridging surface of the channel.

8. The stabilization system of claim 1, wherein the load applied to the elongate member by the fastening mechanism biases the elongate member against the head to fix the tulip with respect to the anchor.

9. The stabilization system of claim 1, wherein the first and second substantially oppositely directed walls are coupled together by a bridging region, the oppositely directed walls cooperate to define a generally U-shaped surface including a partially cylindrical portion in the bridging region; and the volume of the anchor engagement element is defined by a partially curved inner surface that intersects with the channel.

10. The stabilization system of claim 9, wherein the load applied to the elongate member by the locking element biases the elongate member against both the second wall surface and the head of the anchor such that: (i) the elongate member is fixed with respect to the tulip, and (ii) the head is biased against portions of the inner surface of the anchor engagement element to fix the tulip with respect to the anchor.

11. The stabilization system of claim 9, further comprising an aperture extending between the volume of the anchor engagement element and the channel, and defining the intersection of the volume and the channel, wherein the aperture defines a central axis thereof; and wherein the tangential load defines a tangential axis.

12. The stabilization system of claim 11, wherein the tangential axis, the volume of the anchor engagement element, and the aperture are substantially aligned such that the longitudinal axis of the threaded bore intersects the central axis of the aperture.

13. The stabilization system of claim 11, wherein the fastening mechanism is located such that the tangential axis is offset from the volume of the anchor engagement element and the aperture such that the longitudinal axis of the tangential axis is offset from the central axis of the aperture.

14. The stabilization system of claim 1, wherein the tangential load defines a tangential axis and the fastening mechanism is located such that the tangential axis is generally parallel to a central plane of the head of the bone anchor.

15. The stabilization system of claim 1, wherein the tangential load defines a tangential axis and the fastening mechanism is located such that the tangential axis is generally offset from a central plane of the head of the bone anchor.

16. The stabilization system of claim 1, wherein the head of the anchor includes a friction enhancement feature.

17. The stabilization system of claim 16, wherein friction enhancement feature includes at least one of ridges, grooves, protrusions, dimples, crosshatching, and knurling.

18. A stabilization system for implantation in a patient, comprising:
a bone anchor including a head having a contour; and
a tulip including:
(i) a base having an outer surface and an inner surface defining a volume for receiving the head, the contour of the head being of substantially complementary shape such that the tulip may articulate about the head,
(ii) a first opening operable to permit a neck extending from the head to articulate there-within and exit the base through the first opening, and
(iii) a second opening extending through the base transversely with respect to the first opening, and defining a profile including a keyed portion that permits insertion of the head into the volume of the base at substantially one orientation of the head with respect to the profile, and does not permit insertion or removal of the head with respect to the volume of the base in substantially any other orientation of the head with respect to the profile, and
the contour of the head includes at least one keyed surface complementary to the keyed portion of the profile of the second opening such that insertion of the head into the volume of the base is permitted only at substantially one orientation of the head with respect to the profile and the contour of the head and the profile of the second opening are sized such that a shrink fit function is achieved, wherein: (i) at non-equilibrium, insertion of the head into the volume of the base is permitted at at least one orientation of the head with respect to the profile, and (ii) at equilibrium, insertion or removal of the head with respect to the volume of the base in substantially any orientation of the head with respect to the profile is prohibited.

19. A stabilization system for implantation in a patient, comprising:
a bone anchor including a head having a contour; and
a tulip including:
(i) a base having an outer surface and an inner surface defining a volume for receiving the head, the contour of the head being of substantially complementary shape such that the tulip may articulate about the head,
(ii) a first opening operable to permit a neck extending from the head to articulate there-within and exit the base through the first opening, and
(iii) a second opening extending through the base transversely with respect to the first opening, and defining a profile including a keyed portion that permits insertion of the head into the volume of the base at substantially one orientation of the head with respect to the profile, and does not permit insertion or removal of the head with respect to the volume of the base in substantially any other orientation of the head with respect to the profile, and
the contour of the head includes at least one keyed surface complementary to the keyed portion of the profile of the second opening such that insertion of the head into the volume of the base is permitted only at substantially one orientation of the head with respect to the profile, a plug element operatively connectable to the head after insertion into the volume of the tulip, the plug being operable to alter the keyed surface of the head such that removal of the head with respect to the volume of the base in substantially any orientation of the head with respect to the profile of the opening is prohibited.

20. A stabilization system for implantation in a patient, comprising:
a bone anchor including a head having a contour; and
a tulip including:
(i) a base having an outer surface and an inner surface defining a volume for receiving the head, the contour of the head being of substantially complementary shape such that the tulip may articulate about the head, (ii) a first opening operable to permit a neck extending from the head to articulate there-within and exit the base through the first opening, and (iii) a second opening extending through the base transversely with respect to the first opening, and defining a profile including a keyed portion that permits insertion of the head into the volume of the base at substantially one orientation of the head with respect to the profile, and does not permit insertion or removal of the head with respect to the volume of the base in substantially any other orientation of the head with respect to the profile, and the contour of the head includes at least one keyed surface complementary to the keyed portion of the profile of the second opening such that insertion of the head into the volume of the base is permitted only at substantially one orientation of the head with respect to the profile, a plug operatively connectable to the head and including a complimentary contour, wherein the profile of the second opening permits insertion of the head without the plug into the volume of the base, and does not permit insertion or removal of the head, with the plug, into or from the volume of the base.

21. The stabilization system of claim 20, wherein: the head includes a first partial spherical contour; and the complimentary contour of the plug includes a second partially spherical contour that at least increases the first spherical contour of the head when coupled thereto.

22. The stabilization system of claim 21, wherein: the first partial spherical contour of the head defines a first cut-off spherical contour including a first substantially planar surface; and the second partial spherical contour of the plug defines a second cut-off spherical contour including a second substantially planar surface.

23. The stabilization system of claim 22, wherein the profile of the second opening of the base corresponds to a cross section of the head taken perpendicularly through the first substantially planar surface.

24. The stabilization system of claim 23, wherein the cross section is taken through a plane of maximal diameter of the head.

25. The stabilization system of claim 22, wherein: one of the first and second substantially planar surfaces includes a bore and the other of the first and second substantially planar surfaces includes a mating post; and the plug is operatively coupled to the head by engaging the post into the bore.

26. The stabilization system of claim 20, wherein the profile of the second opening of the base is sized and shaped to: (i) permit the head to slide therethrough into the volume when in a first orientation, (ii) prevent the head from leaving the volume when in other orientations, and (iii) prevent the head coupled with the plug from leaving the volume when in any orientation.

27. The stabilization system of claim 26, wherein at least one of: the profile of the second opening of the base is sized and shaped to permit the plug to pass therethrough and couple to the head after the head has been received in the volume; and the first opening is sized and shaped to permit the plug to pass therethrough and couple to the head after the head has been received in the volume.

28. The stabilization system of claim 26, wherein: the tulip includes a channel operable to receive a stabilization rod; the volume of the base is defined by the inner surface that intersects with the channel defining an aperture therebetween; and the aperture is sized and shaped to permit the plug to pass therethrough and couple to the head after the head has been received in the volume.

29. The stabilization system of claim 18, wherein the first and second openings communicate with one another to permit the neck of the head to extend through either of the openings depending on the orientation of the neck with respect to the tulip.

30. The stabilization system of claim 18, comprising one or more further openings extending through the base transversely with respect to the first opening and at least partially communicating with the first opening to permit the neck of the bone anchor to enter the further opening in one or more articulation positions.

31. The stabilization system of claim 30, wherein at least two of the further openings are disposed on opposite sides of the base.

32. The stabilization system of claim 30, wherein the second opening and the at least one further opening are disposed substantially equidistant from the other about the base.

33. The stabilization system of claim 20, wherein at least one of the head and the plug of the anchor include a friction enhancement feature.

34. The stabilization system of claim 33, wherein friction enhancement feature includes at least one of ridges, grooves, protrusions, dimples, crosshatching, and knurling.

* * * * *